United States Patent [19]

Kuhn et al.

[11] Patent Number: 5,459,276
[45] Date of Patent: Oct. 17, 1995

[54] BENZAZOLYLCOUMARIN-BASED ION INDICATORS FOR HEAVY METALS

[75] Inventors: Michael A. Kuhn; Richard P. Haugland; Brian M. Hoyland, all of Eugene, Oreg.

[73] Assignee: Molecular Probes, Inc., Eugene, Oreg.

[21] Appl. No.: 246,847

[22] Filed: May 20, 1994

[51] Int. Cl.$^6$ .................. G01N 33/52; C07D 417/04; C07D 407/04

[52] U.S. Cl. .................. 548/159; 436/74; 436/800; 548/217; 548/304.7

[58] Field of Search .................. 548/159, 217, 548/304.7; 436/74, 800

[56] References Cited

U.S. PATENT DOCUMENTS

| | | |
|---|---|---|
| 4,544,496 | 10/1985 | Claussen et al. |
| 4,603,209 | 7/1986 | Tsien et al. |
| 4,849,362 | 7/1989 | DeMarinis et al. |
| 5,049,673 | 9/1991 | Tsien et al. |

OTHER PUBLICATIONS

G. Guilbault, Practical Fluoresence, 2nd Ed., Marcel Dekker, Inc., New York, 1990.
Tsien, Biochemistry, 19, 2396 (1980).
Tsien, *Intracellular Measurements of Ion Activities*, Ann. Rev. Biophys. Bioeng., 12, 91 (1983).
Smith et al., J. Chem. Soc. Perkin Trans., 2 1195 (1993).
Haugland, Molecular Probes Handbook of Fluorescent Probes and Research Chemicals Set 20 (1992).
Pethig, et al., Cell Calcium, 10, 491 (1989).
Iatridou et al., Cell Calcium, 15, 190 (1994).
Akkay et al., Biophys. J. 66, A162 (1994).
Bioprobes 18 (1993).
Wolfbeis et al., Bull. Chem. Soc. Jpn. 58, 731 (1994).
Etter et al., J. Biol. Chem. 269, 10141 (1994).

*Primary Examiner*—Robert Gerstl
*Attorney, Agent, or Firm*—Allegra J. Helfenstein; Anton E. Skaugset

[57] ABSTRACT

The indicator compounds of the present invention are substituted or unsubstituted 5'-nitro-BAPTA chelators that contain a benzazolyl-coumarin substructure, and the pharmaceutically acceptable non-toxic salts and esters thereof. These compounds are useful for the detection and quantification of polycationic metal ions, particularly $Zn^{2+}$, $Pb^{2+}$, $Ba^{2+}$, $Cd^{2+}$, $Hg^{2+}$ and $La^{3+}$.

The compounds of the invention have the structure:

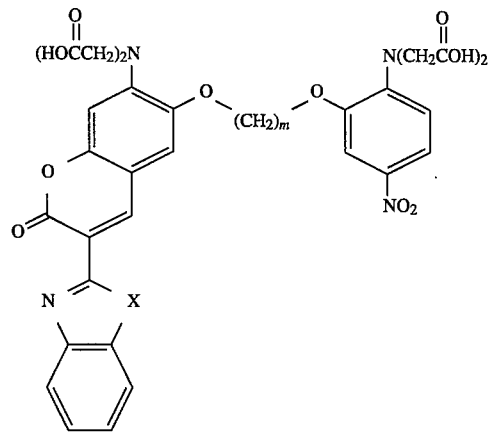

where m=2 or 3 and X can be S, O, or $C(CH_3)_2$; optionally substituted by substituents that alter the binding affinity of the indicator, shift the spectral properties of the indicator, or act as a reactive site for the preparation of a variety of conjugates.

16 Claims, 7 Drawing Sheets

BENZAZOLYLCOUMARIN-BASED ION INDICATORS FOR HEAVY METALS

This invention was made with U.S. Government support under research contract no. N00014-93-C-0270 awarded by the U.S. Office of Naval Research. The U.S. Government has certain rights in this invention.

FIELD OF THE INVENTION

This invention relates to fluorescent chelating indicators that selectively bind to polyvalent metal ions. In particular, the invention relates to fluorescent benzothiazolyl-, benzoxazolyl- or indolyl-substituted coumarin-based 5'-nitro-BAPTA chelators that are used to detect and quantify heavy metal ions, including zinc, lead, barium, cadmium and mercury ions.

BACKGROUND OF THE INVENTION

Metals play an important role in biological systems in regulating enzyme activity, protein structure, and cellular signaling. Metals can also have a deleterious effect when present in excess of bodily requirements or capacity to excrete and, if not usually present in cells may be highly toxic to the cell. Metals, and in particular heavy metals such as zinc ($Zn^{2+}$), lead ($Pb^{2+}$), barium ($Ba^{2+}$) cadmium ($Cd^{2+}$) and mercury ($Hg^{2+}$) are also significant environmental contaminants. A large number of natural and synthetic materials are known to selectively or non-selectively bind to or chelate metals. Ion chelators are commonly used in solution for in vivo control of ionic concentrations and detoxification of excess metals, and as in vitro buffers. When bound to a fluorophore, ion chelators can often be used as optical indicators of ions.

Numerous chromophoric or fluorescent complexing agents for metals, including heavy metals, have been described (see in particular G. Guilbault, PRACTICAL FLUORESCENCE, 2nd Ed., Marcel Dekker, Inc., New York, 1990). A number of indicators whose fluorescence responds to physiological ranges of $Ca^{2+}$ have been described, including our copending application BENZAZOLYLCOUMARIN-BASED ION INDICATORS, filed May 20, 1994. Many of these indicators are fluorescent derivatives of the BAPTA chelators originally described by Tsien (Tsien, BIOCHEMISTRY 19, 2396 (1980)). Examples of BAPTA-based fluorescent indicators include quin-2 (Tsien, BIOCHEMISTRY supra); fura-2, and indo-1 (U.S. Pat. No. 4,603,209 to Tsien et al., 1986); fluo-3 an rhod-2 (U.S. Pat. No. 5,049,673 to Tsien et al. 1991); FURA-RED (Molecular Probes, Inc., Eugene, OR, trademark for 1-[6-amino-2(5-oxo-2-thioxo-4-thiazolidinylidene)methyl-5-benzofuranyoxy]-2-2-(2'-amino-5'   -methyl-phenoxy-)ethane-N,N,N',N'-tetraacetic acid and the tetraacetoxymethyl ester thereof, U.S. Pat. No. 4,849,362 to DeMarinis, et al. 1989). Additional BAPTA-based fluorescent indicators for $Ca^{2+}$ have been described by Tsien (*Intracellular Measurements of Ion Activities*, ANN. REV. BIOPHYS. BIOENG., 12, 91 (1983)), and Smith et al., (J. CHEM. SOC. PERKIN TRANS. 2, 1195 (1993)). Other BAPTA-based indicators are described in Copending application REACTIVE DERIVATIVES OF BAPTA USED TO MAKE ION-SELECTIVE CHELATORS, Ser. No. 07/843, 360 (filed Feb. 25, 1992) by Kuhn et al.

The complexation of $Zn^{2+}$ is known to enhance the fluorescence of certain BAPTA-based indicators such as fura-2 and to shift the indicator's excitation spectrum. Although fura-2 has much higher affinity for $Zn^{2+}$ than do the indicators of the present invention (dissociation constants for $Zn^{2+}$ complexes of fura-2 are typically in the nM range, rather than in the μM range as for the instant indicators), the higher affinity of fura-2 for $Ca^{2+}$ in particular makes it difficult to measure other metals such as $Zn^{2+}$ and $Pb^{2+}$ in the presence of physiological concentrations of $Ca^{2+}$ ($10^{-8}$ to $10^{-5}$ M free $Ca^{2+}$) or $Mg^{2+}$ ($10^{-4}$ to $10^{-2}$ M free $Mg^{2+}$). Furthermore, the excitation spectra of fura-2 and its $Zn^{2+}$ complex is in the ultraviolet range, where quartz optics are typically needed for detection, and where intrinsic cellular autofluorescence is generally very high. An indicator capable of detecting and quantifying $Zn^{2+}$, that is also insensitive to $Ca^{2+}$, is therefore needed.

The indicators described in copending application BENZAZOLYLCOUMARIN-BASED ION INDICATORS (filed May 20, 1994) are less sensitive to $Ca^{2+}$ than previously described BAPTA-type indicators. However, these lower-affinity indicators are largely insensitive to heavy metal ions. Substitution at the 5' position of the BAPTA chelator by nitro is known to reduce the affinity of BAPTA-based indicators for $Ca^{2+}$ (e.g. see Calcium Green™-5N versus Calcium Green™-1 in Haugland, MOLECULAR PROBES HANDBOOK OF FLUORESCENT PROBES AND RESEARCH CHEMICALS, Set 20 (1992) and Pethig, et al., CELL CALCIUM 10, 491 (1989)). However, substitution by nitro at the 5'-position of the above-described low-affinity indicators almost totally quenches the fluorescence of the free (non-complexed) indicator, even though the benzazole fluorophore is bound to the opposite ring of the BAPTA chelator.

Surprisingly, the substituted of a 5'-nitro group results in a family of indicators that respond to the complexation of a variety of heavy metal ions, including the heavy metal ions $Zn^{2+}$, $Pb^{2+}$, $Ba^{2+}$, $Cd^{2+}$, $Hg^{2+}$ and $La^{3+}$. This result is particularly unexpected because $Pb^{2+}$, $Cd^{2+}$ and $Ba^{2+}$ have been reported to strongly que other BAPTA-type indicators (Haugland, MOLECULAR PROBES HANDBOOK, supra, Set 20, pg. 113 (1992)). Furthermore, the instant indicators give a distinct maximum emission intensity and a specific range of sensitivity ($K_d$) upon binding different metal ions that could be used, in principle, to detect the concentration of more than one metal ion simultaneously. The present indicators exhibit virtually no fluorescence response to the binding of either $Ca^{2+}$ or $Mg^{2+}$. Consequently, substitution of a 5'-nitro on the benzazolylcoumarin-based BAPTA ion indicators yields a family of indicators that is typically not useful for measuring physiologically relevant levels of $Ca^{2+}$ or $Mg^{2+}$.

The compounds of the present invention possess special utility for the detection and quantification of $Zn^{2+}$ ions. The currently utilized $Zn^{2+}$ ion probe N-(6-methoxy-8-quinolyl)-p-toluenesulfonamide (TSQ) has been used to detect $Zn^{2+}$ in physiological studies. TSQ binds $Zn^{2+}$ so strongly that it is insensitive to small changes in equilibrium levels of $Zn^{2+}$. The instant compounds represent the first practical equilibrium indicators for intracellular $Zn^{2+}$ that are useful in the submicromolar range.

The compounds of the present invention have significant utility as a means of detecting and quantifying certain metal ion levels in living cells, biological fluids or aqueous solutions. The relatively long wavelength excitation and emission bands of the compounds of the present invention enable their use with a variety of optical devices and require no specialized (quartz) optics, such as are required by indicators that are excited or that emit at shorter wavelengths.

DESCRIPTION OF THE INVENTION

Figure 1:
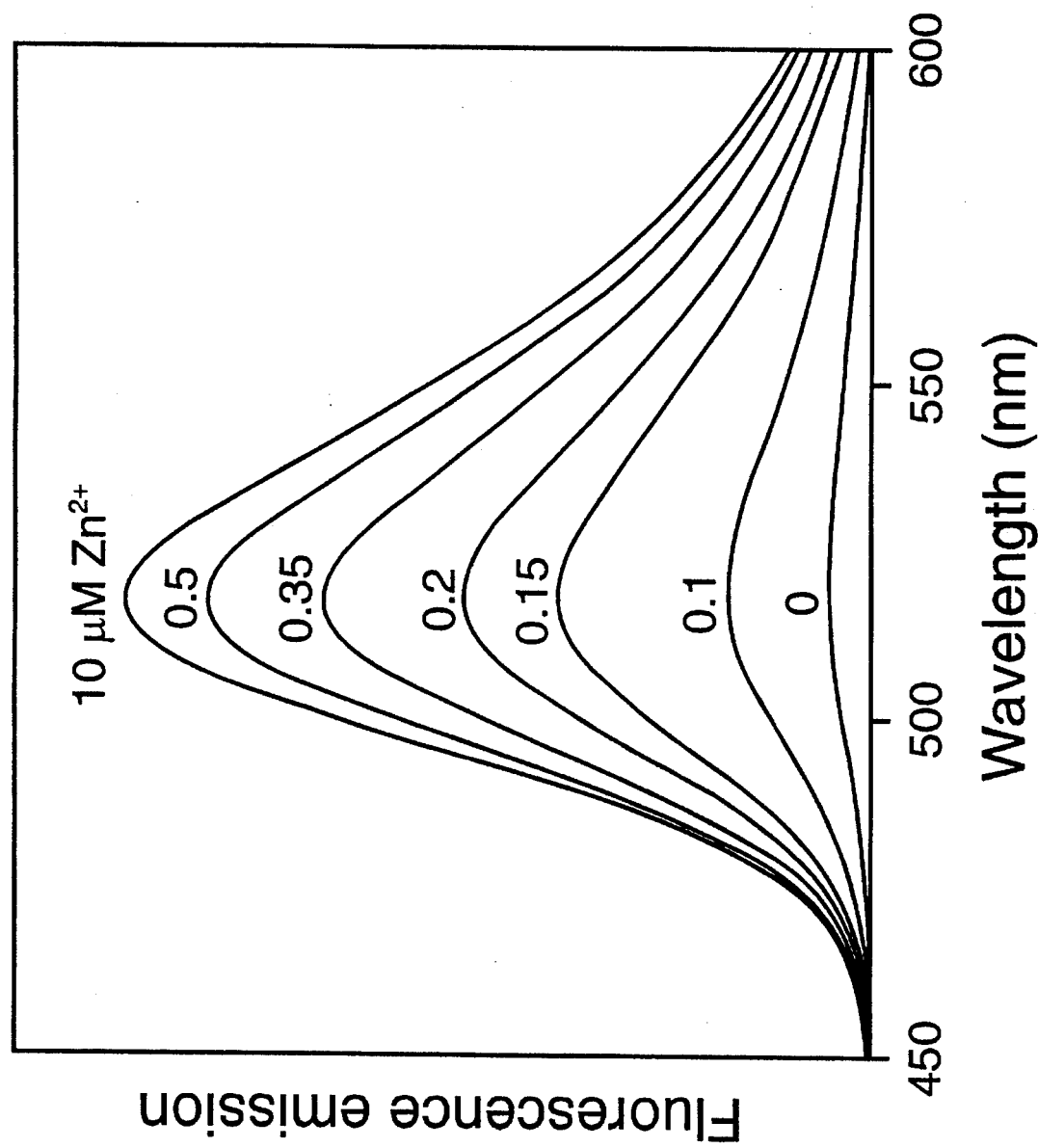
FIG. 1: The effect of increasing $Zn^{2+}$ concentration on the excitation spectrum of Compound 4. Free $Zn^{2+}$ concentrations range from 0 to 10 µM as described in Example 8.
Figure 2:
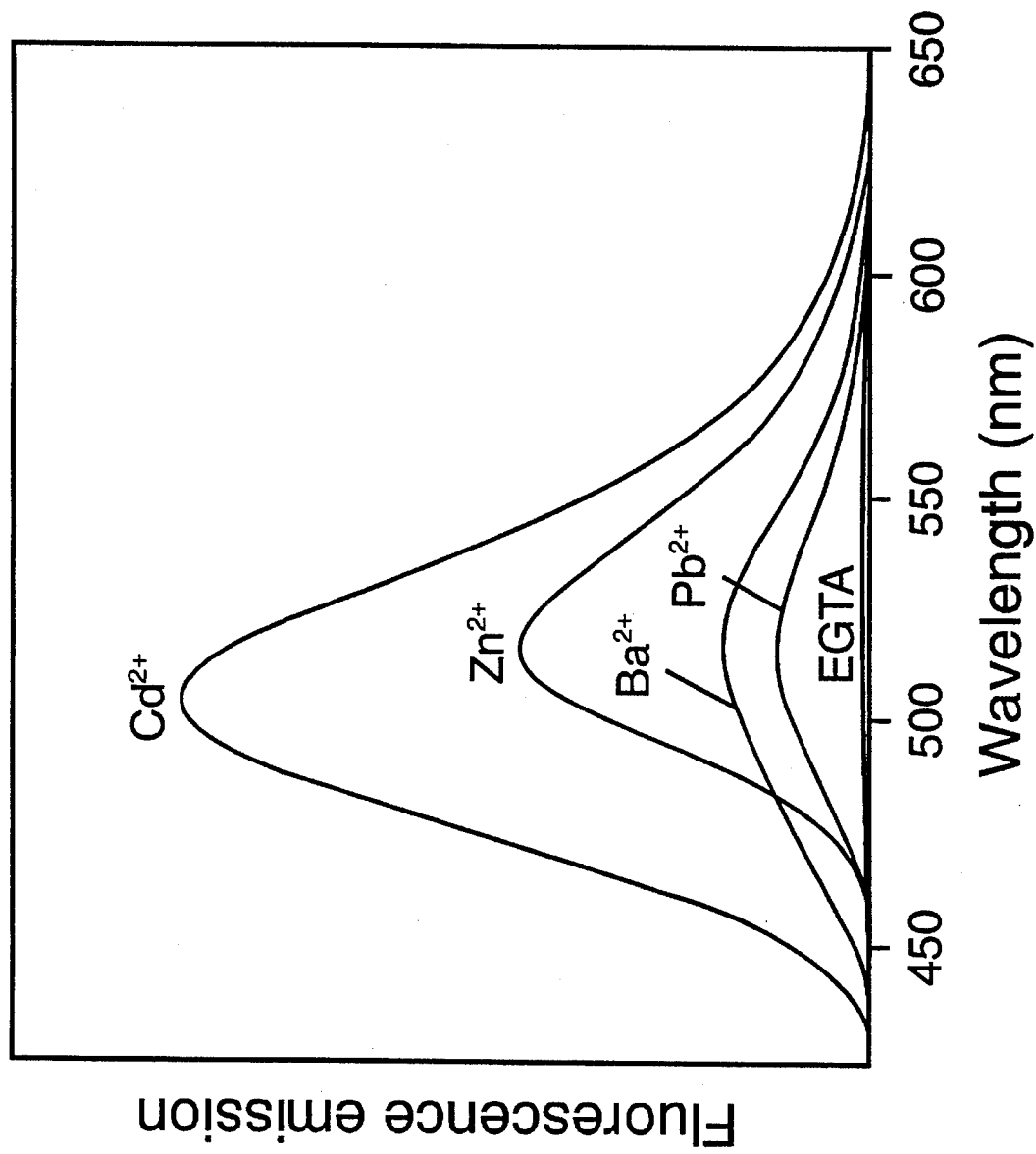
FIG. 2: The fluorescence emission spectrum of Compound 4 in 25 µM solutions of $Cd^{2+}$, $Zn^{2+}$, $Ba^{2+}$, $Pb^{2+}$ and in 10 mM EGTA (Example 9, Table 1).
Figure 3:
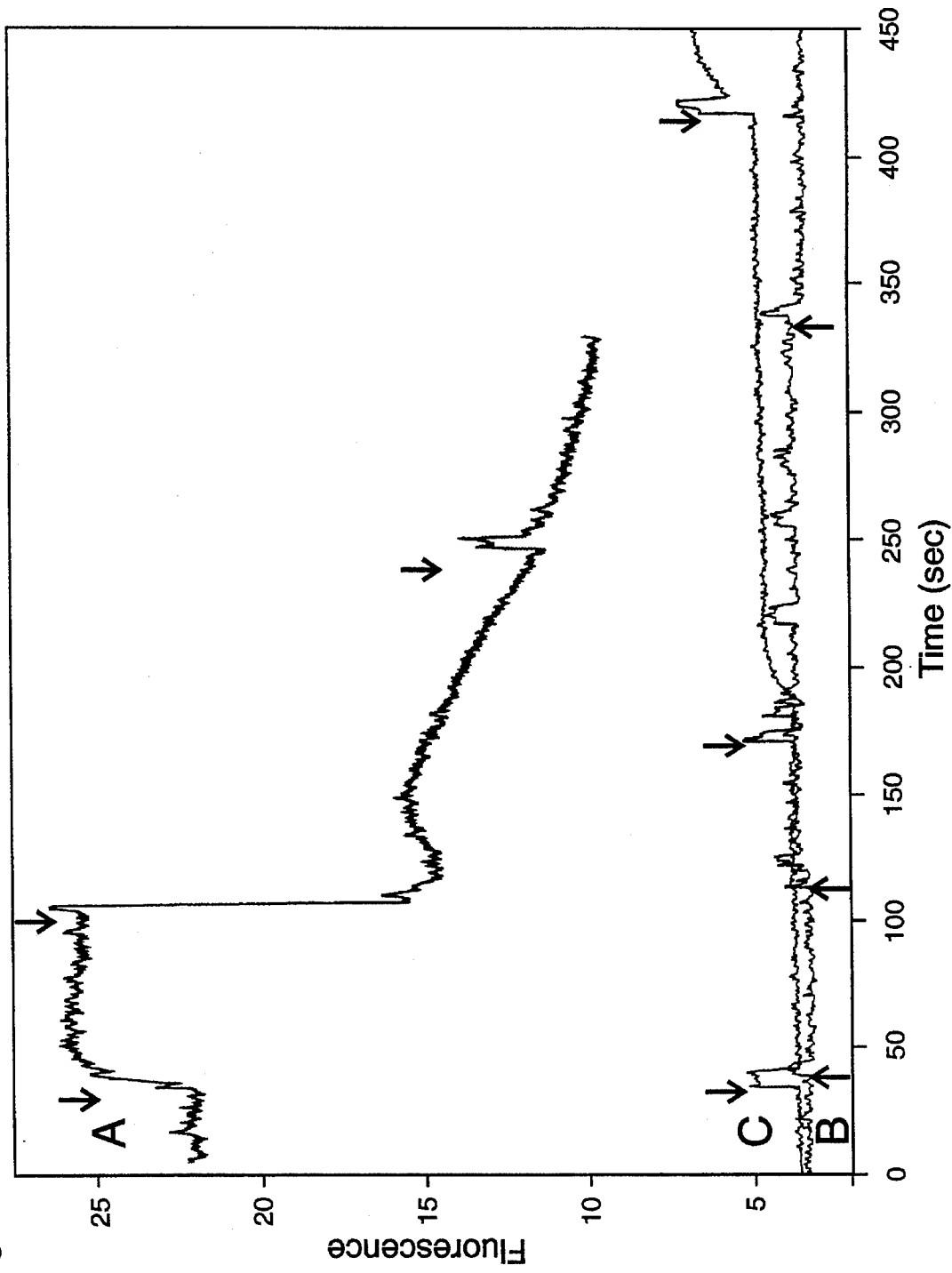
FIG. 3: The time course of the intracellular $Zn^{2+}$ response of Compound 5 for 7.5 minutes after loading in cells, as described in Example 10. Time course A shows the response of intracellular fura-2 while time courses B and C show the response of Compound 5. Additions are made at times indicated by arrows as follows: (A) 2 µM Br-A23187, 200 µM $ZnCl_2$, 50 mm $CaCl_2$. (B) 2 µM Br-A23187, 200 µM $ZnCl_2$, 2 mM EDTA/4 mM Tris base. (C) 2 µM Br-A23187, 1 µM $ZnCl_2$, 0.1% Triton®X-100.

The indicator compounds of the present invention are BAPTA-type chelators that are substituted at the 5'-position by nitro, and that contain a benzazolyl-coumarin substructure, and the pharmaceutically acceptable non-toxic salts and esters thereof. The compounds of the present invention possess utility as indicators for heavy metal ions in aqueous solution, including $Zn^{2+}$, $Pb^{2+}$, $Ba^{2+}$, $Cd^{2+}$, $Hg^{2+}$ and $La^{3+}$. The invention are represented by the following general formula:

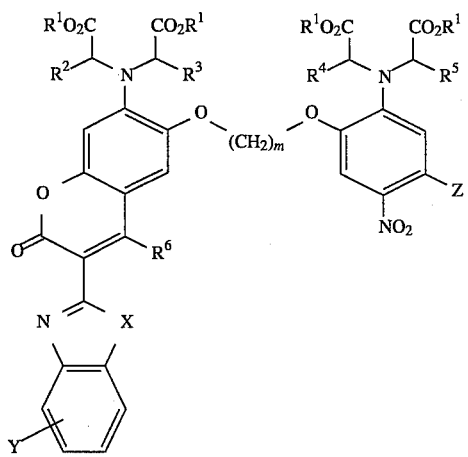

The subscript m is either 2 or 3, giving either an ethylidene or propylidene bridge. Preferably, m is 2.

$R^1$ is H, an alkyl group having 1–5 carbons, a benzyl, an alpha-acyloxyalkyl or a pharmaceutically acceptable esterifying group, a t-butyldimethylsilyl ester, or a pharmaceutically acceptable salt. Typically $R^1$ is H, an alkali metal ion or an acetoxymethyl ester.

As used herein, pharmaceutically acceptable salts are non-toxic salts of carboxylic acids known and used in the pharmaceutical industry. Examples include $K^+$, $Na^+$, $Cs^+$, $Li^+$, $Ca^{2+}$, $Mg^{2+}$, $NR_4^+$ salts, where R=H, $C_1$–$C_4$ alkyl, or $C_2$–$C_4$ alkanol or combinations thereof, or combinations of acid salts of these counterions plus free acid groups. Pharmaceutically acceptable esterifying groups are those that form readily hydrolyzable esters which are known and used in the pharmaceutical industry, such as α-acyloxyalkyl esters, especially acetoxymethyl ($CH_3CO_2CH_2$—) esters.

The use of esterification to protect carboxylate groups improves the solubility of the indicator in organic solvents. Appropriate ester groups also allow the indicator to more freely permeate cellular membranes. In particular, chelators that are protected by acetoxymethyl esters penetrate cell membranes, whereupon intracellular esterases cleave the esters hydrolytically, producing the free indicator within the cell.

$R^2$, $R^3$, $R^4$ and $R^5$ are independently H or methyl. Substitution of methyl at one or more of $R^2$, $R^3$, $R^4$ and $R^5$ can be used to modify the affinity, and to a certain extent, the selectivity, of the indicator for specific metal ions (Smith et al., supra). Preferably, $R^2$–$R^5$ are H.

$R^6$ is H, CN, $CH_3$, $CF_3$ or $CONH_2$. Preferably, $R^6$ is H or CN. The substitution of cyano (—CN) or trifluoromethyl ($CF_3$) substituents at the 4-position of structurally related coumarin fluorophores shifts the absorption of those fluorophores to significantly longer wavelengths (for example, U.S. Pat. No. 4,544,496 to Claussen et al.).

X is either O, S, or $C(CH_3)_2$, forming a benzoxazole, benzothiazole, or indole heterocycle, respectively. These are collectively referred to herein as benzazoles and, when attached to the coumarin through their 2-positions, are collectively referred to as "2-benzazolyl" moieties or substituents. The preferred benzazole heterocycles are benzoxazoles or benzothiazoles. In all embodiments of the invention, there is extensive electron delocalization throughout the coumarin substructure and the attached heterocycle. This delocalization enables embodiments of the invention to possess absorbance and fluorescent emission bands that occur at longer wavelengths than those possessed by a BAPTA chelator bound directly to a benzazole fluorophore, or a coumarin fluorophore, only.

Each benzazole substituent is substituted further by Y, where Y is H, an alkyl having 1-18 carbons, —$NO_2$, —$NH_2$, —NH(C=O)$(CH_2)_n CH_3$ (n=0–16), —CF, F, Cl, Br, I, —$OR^8$, —$CO_2R^9$, or —$OCH_2CO_2R^9$; where $R^8$ and $R^9$ are as defined previously. Alternatively, Y is a covalently attached conjugant. Preferably, Y is H, carboxylate, an acetoxymethyl ester of carboxylate or a covalently attached conjugant, more preferably Y is H. Preferred ring positions for the substituent Y are the 5- and 6-positions of the benzazole ring system.

The substituent Z is H, an alkyl having 1-18 carbons, —$NH_2$, —NH(C=O)$(CH_2)_n CH_3$ (n=0–16), —$CF_3$, F, Cl, Br, I, —$OR^8$, —$CO_2R^9$, or —$OCH_2CO_2R^9$; where $R^8$ is H, an alkyl group having 1-18 carbons, a benzyl ($C_6H_5CH_2$—), an alpha-acyloxyalkyl, an acetate, or a t-butyldimethylsilyl ether; and $R^9$ is H, an alkyl group having 1-17 carbons, a benzyl ($C_6H_5CH_2$—) an alpha-acyloxalkyl or other pharmaceutically acceptable esterifying group, a t-butyldimethylsilyl ester, or a pharmaceutically acceptable salt. Alternatively, Z is a covalently attached conjugant. Preferably, Z is H, methyl, —$NH_2$ or a covalently attached conjugant. Typically Z is H.

As used herein, a conjugant is a molecule or substance that when attached to the indicator forms an indicator-conjugate. Selected conjugants include, but are not limited to, antibodies, amino acids, proteins, peptides, polypeptides, enzymes, enzyme substrates, hormones, lymphokines, metabolites, antigens, haptens, lectins, avidin, streptavidin, toxins, poisons, environmental pollutants, carbohydrates, oligosaccharides, polysaccharides, glycoproteins, glycolipids, nucleotides, oligonucleotides, nucleic acids and derivatized nucleic acids (including deoxyribo- and ribonucleic acids), DNA and RNA fragments and derivatized fragments (including single and multi-stranded fragments), natural and synthetic drugs, receptors, virus particles, bacterial particles, virus components, biological cells, cellular components (including cellular membranes and organelles), natural and synthetic lipid vesicles, polymers, polymer particles, polymer membranes, and glass and plastic surfaces and particles.

Preferably the covalently attached conjugant is a polymer film or a polymer microparticle, wherein the polymer is polyacrylamide, or the covalently attached conjugant is a dextran, a modified dextran or glass. Where the conjugant is a polymer microparticle, the particle is typically spherical or nearly spherical and the particle size is typically greater than 0.01 μm and less than 50 μm. Where the conjugant is a dextran, the dextran typically has a molecular weight greater than 1000 and less than 1,000,000. Attachment of the indicator to a polymeric material can be used to impart ion-sensing properties on that material and to solubilize, insolubilize or otherwise modify the properties of the indicator, the polymer, or both.

The desired indicator-conjugate is most easily prepared when the indicator is initially substituted at Y or Z by amino ($NH_2$), $-CO_2H$, or $-OCH_2CO_2H$. These substituents can be readily converted to a reactive derivative that is easily attached to polymers, lipids, members of specific binding pairs or other materials. The appropriate reactivities and procedures to prepare the reactive indicators and conjugates is completely described in copending application 07/843, 360 (supra).

SYNTHESIS

Useful precursors for preparation of the compounds in this invention have been described in U.S. Pat. Nos. 4,603,209 (supra), 5,049,673 (supra) and 4,849,362 (supra).

Figure 4:
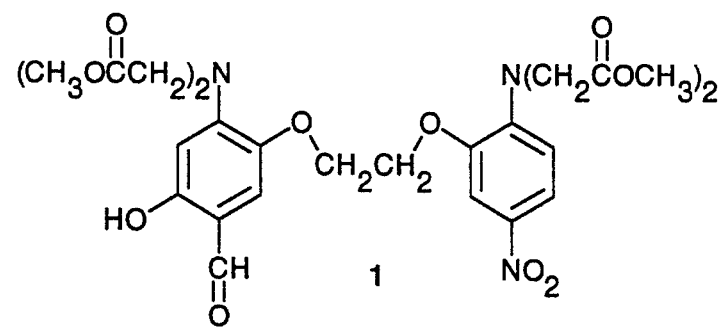
FIG. 4: Synthetic scheme for preparation of Compound 3, as described in Example 1.
Figure 4:
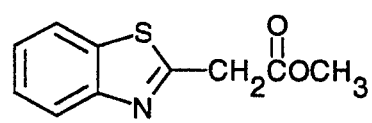
Figure 4:
Figure 4:
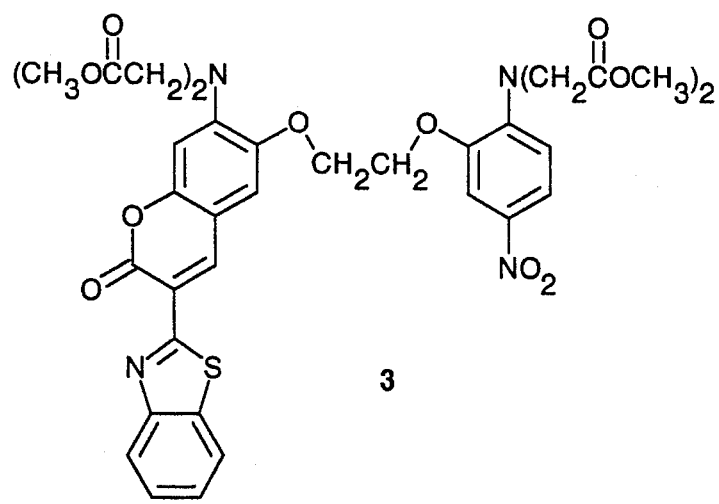
Figure 5:
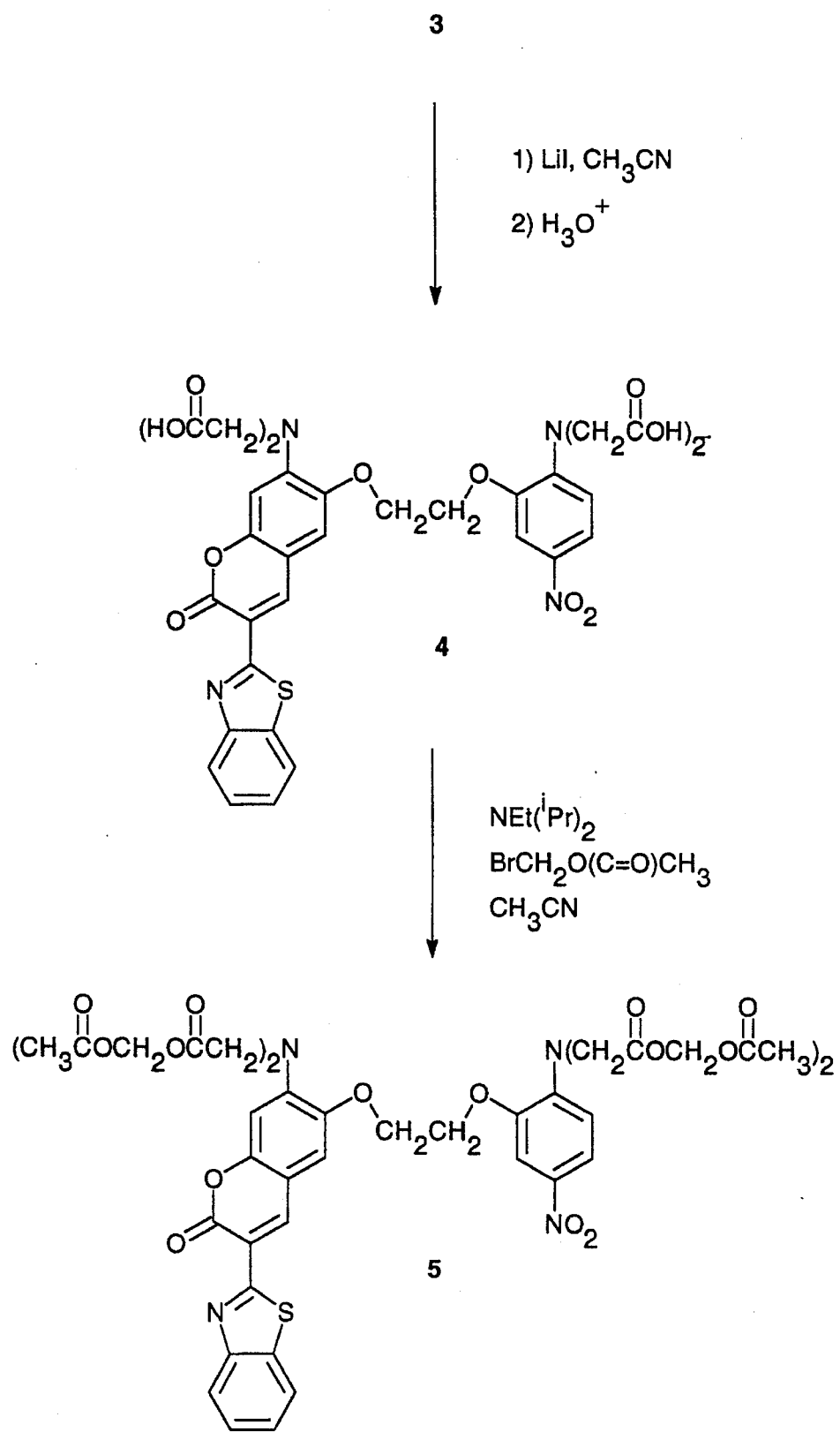
FIG. 5: Synthetic scheme for preparation of Compounds 4 and 5, as described in Examples 2 and 3.

The compounds of the present invention are generally prepared from 4-hydroxy-5-formyl-5'-nitro BAPTA tetramethyl ester (Compound 1). Condensation of 1 with the methyl ester of benzothiazole (2) gives the fluorescent benzothiazole-coumarin (BTC) 5'-nitro-BAPTA derivative in high yield (3) (FIG. 4, Example 1). As the coumarin fluorophore is sensitive to strongly basic conditions, the hydrolysis of the methyl esters protecting the tetracarboxylate chelate is effected using LiI in acetonitrile (FIG. 5). The tetralithium salt is water-soluble, and can be precipitated as the free acid (4) or purified by reverse phase chromatography in dilute LiOH, followed by lyophilization.

Figure 6:
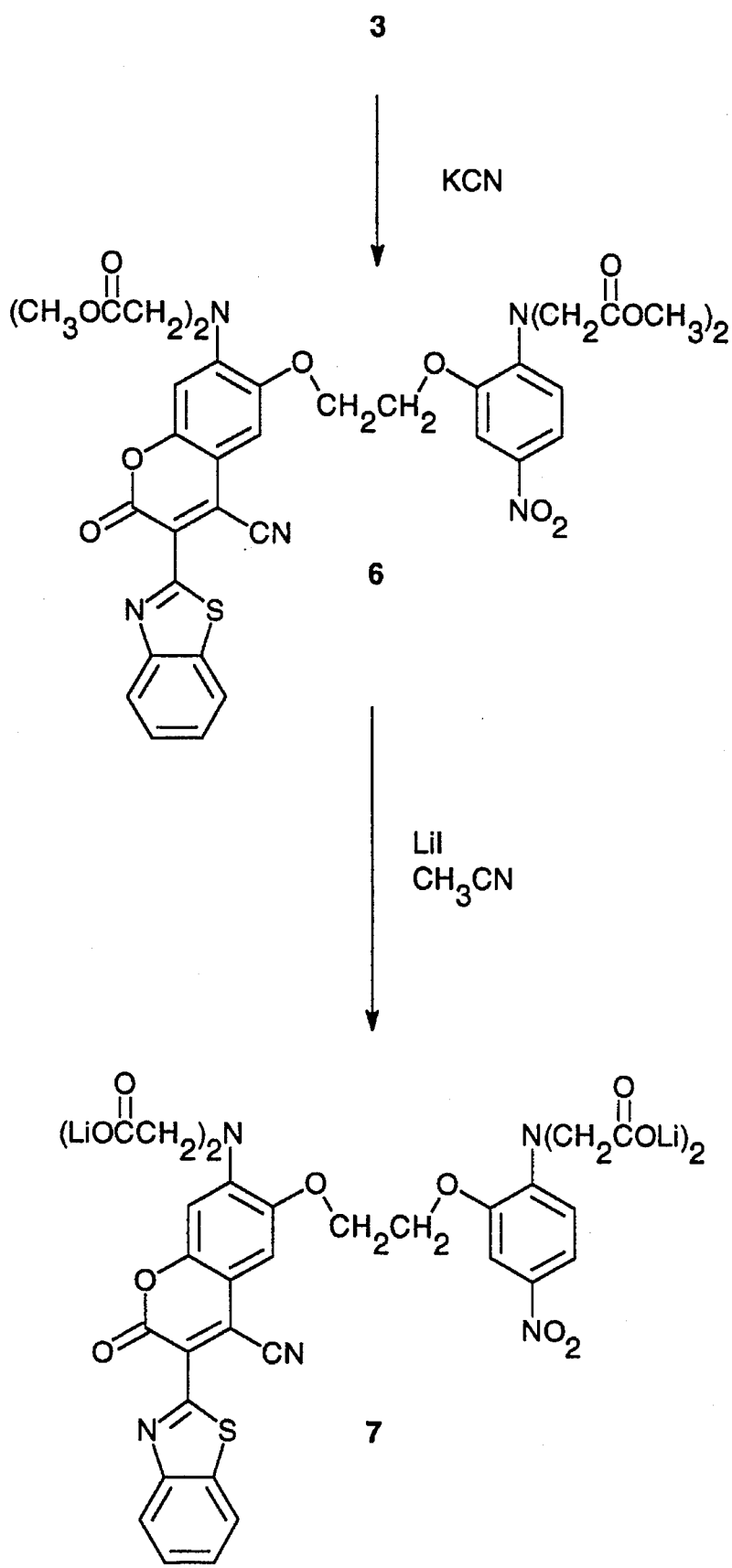
FIG. 6: Synthetic scheme for preparation of Compounds 6 and 7, as described in Examples 4 and 5.
Figure 7:
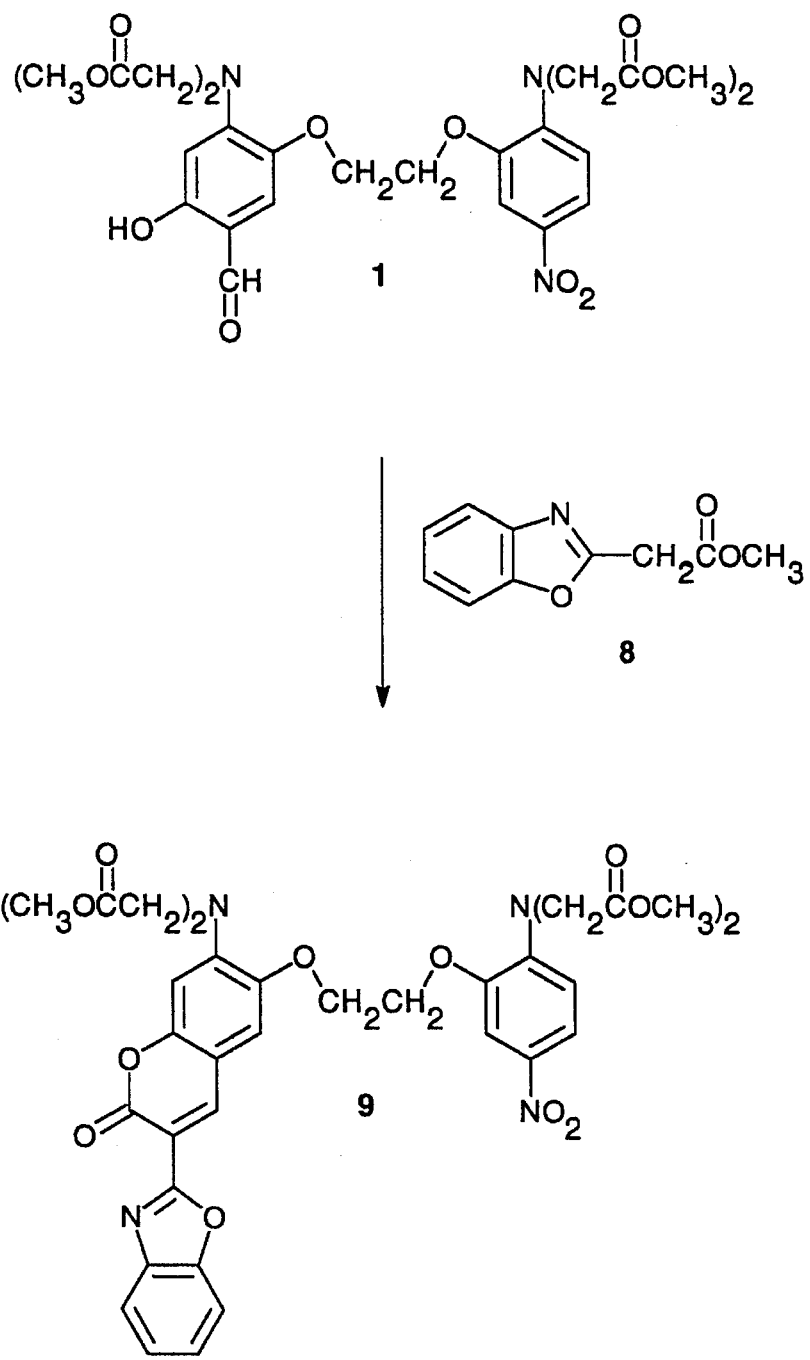
FIG. 7: Synthetic scheme for preparation of Compound 9, as described in Example 6.

Reaction of BTC 5'-nitro-BAPTA (3) with KCN yields the cyano-substituted BTC 5'-nitro-BAPTA, tetramethyl ester (6) (FIG. 6, Example 4). Cleavage of the methyl esters in LiI is similar to that described for BTC 5'-nitro-BAPTA (Example 5, Compound 7).

Introduction of a methyl group on the iminodiacetic acids involved in metal chelation has the effect of increasing the affinity of the BAPTA chelate for $Ca^{2+}$ (Smith et. al., supra). This method can be used to make coumarin-based ion indicators with a range of affinities for free polyvalent metal ions. Two methyl groups can be introduced next to the chelating acids by two sequential alkylations. The diamine is reacted with two equivalents of methyl bromoacetate to give the bis-methyl ester, which is isolated and treated with methyl 2-bromopropionate at a higher temperature in the presence of a stronger base to give the tetraester. Modifications of this strategy could give one, two, three or four methyl groups on the iminodiacetic acid groups of the BAPTA chelator, resulting in a series of indicators with increased affinity for divalent cations when compared with the parent indicator, BTC 5'-nitro-BAPTA.

METHOD OF USE

In order to be useful as an indicator, the fluorescent properties of the chelator must exhibit some change upon complexation of the desired metal ion in the polycarboxylate chelate. Upon binding heavy metal ions, the compounds of the present invention display a shift in the absorption spectrum to shorter wavelength, and an increase in fluorescence emission when excited at or near the absorption maximum of the ion-indicator complex. Excitation of the ion-indicator complex gives a linear increase in emission intensity that is directly related to the concentration of free metal ion in the indicator solution (Example 8, FIG. 1). The emission intensity at saturating ion levels is characteristic of the target ion. As the fluorescence response of the present indicators is related to the equilibrium concentration of the target metal ion, the response time to concentration transients is short. The instant compounds do not exhibit such enhancement upon binding $Ca^{2+}$ or $Mg^{2+}$ ions.

The specific indicator used in an assay or experiment is selected based on the desired affinity for the target ion as determined by the expected concentration range in the sample, the desired spectral properties, and the desired selectivity of the indicator. Initially, the suitability of a material as an indicator for detection of a target ion concentration is commonly tested by mixing a constant amount of the indicating reagent with a measured amount of the target ion under the expected experimental conditions.

Preferred indicators display a high selectivity, that is, they show a high rejection of non-target ions. This ability to detect a non-target ion can be tested by a comparable titration of the indicator with that ion. Although $Zn^{2+}$, $Pb^{2+}$, $Ba^{2+}$, $Cd^{2+}$, $Hg^{2+}$ and $La^{3+}$ are the preferred target ions, other tar quantified with the compounds of the present invention are shown in Table 1, which depicts the fluorescence response of Compound 4 in the presence of 25 μM solutions of selected heavy metals. Additionally, any ion that yields a detectable change in absorption wavelengths, excitation wavelengths, emission wavelengths, fluorescence lifetimes or other measurable spectral property over the concentration range of interest is a useful target ion (see Table 1). The detectable change in a given spectral property can be either an increase or a decrease. However, spectral changes that result in an enhancement of fluorescence intensity are preferred.

TABLE 1

Fluorescence Response to Selected Target Heavy Metal Ions

| Target Ion | Emission Maximum (nm) | Relative Intensity |
|---|---|---|
| $Cd^{2+}$ | 503 | 1.0 |
| $Hg^{2+}$ | 505 | 0.56 |
| $Zn^{2+}$ | 515 | 0.44 |
| $La^{3+}$ | 519 | 0.37 |
| $Ba^{2+}$ | 518 | 0.18 |
| $Tb^{3+}$ | 524 | 0.15 |
| $Pb^{2+}$ | 518 | 0.12 |
| $Bi^{3+}$ | 508 | 0.11 |
| $Co^{2+}$ | 510 | 0.10 |
| $Al^{3+}$ | 517 | 0.06 |
| 10 mM EGTA | 528 | 0.02 |

The indicator is generally prepared for use as a detection reagent by dissolving the indicator in solution at a concentration that is adequate for detection of the indicator at the expected concentration of the target ion. Modifications that are designed to enhance permeability of the indicator through the membranes of living cells, such as acetoxymethyl esters and acetates, may require the indicator to be predissolved in an organic solvent such as dimethylsulfoxide (DMSO) before addition to a cell suspension, where the indicators then readily enter the cells. Intracellular enzymes cleave the esters to the more polar acids and phenols that are then well retained inside the cells.

The optical response of the indicating reagent is determined by changes in absorbance or fluorescence intensity, preferably fluorescence emission intensity. If absorbance measurements are used to determine ion concentrations, then it is usually optimal to adjust the optical density of the indicator in the sample over the range of analyte concentration to a value of approximately 0.02 to 2.5 (most preferably 0.1 to 1). For fluorescence measurements, the concentration of the indicator will depend mostly on the sensitivity of the equipment used for its detection.

If the optical response of the indicator will be determined using fluorescence measurements, samples are typically stained with indicator concentrations of $10^{-9}$ M to $10^{-4}$ M. The most useful range of analyte is about one log unit above and below the dissociation constant of the ion-indicator complex. This dissociation constant is determined by titration of the indicator with known concentrations of the target ion, usually over the range of virtually zero concentration to approximately 100 µM of the target ion, depending on which ion is to be measured and which indicator is being used (as in Example 8). The dissociation constant may be affected by the presence of other ions, particularly ions that have similar ionic radii and charge. It may also be affected by other conditions such as ionic strength, pH, temperature, viscosity, presence of organic solvents and incorporation of the sensor in a membrane or polymeric matrix, or conjugation or binding of the sensor to a protein or other biological molecule. Any or all of these effects need to be taken into account when calibrating an indicator.

The indicator is combined with a sample in a way that will facilitate detection of the target ion concentration in the sample. The sample is generally a fluid or liquid suspension that is known or suspected to contain the target ion. Representative samples include intracellular fluids such as in blood cells, cultured cells, muscle tissue, neurons and the like; extracellular fluids in areas immediately outside of cells; in vesicles; in vascular tissue of plants and animals; in biological fluids such as blood, saliva, and urine; in biological fermentation media; in environmental samples such as water, soil, waste water and seawater; and in chemical reactors and bioreactors.

Even in the presence of several metal ions, useful information can often be collected using the indicators of the present invention. For example, the characteristic fluorescence emission of Compound 4 in the presence of saturating amounts of $Cd^{2+}$ is much greater than the fluorescence emission of Compound 4 in the presence of other heavy metal ions. The observation of this characteristically high fluorescence therefore indicates the presence of $Cd^{2+}$, even in the presence of other heavy metal ions. In addition, each target ion has a characteristic binding affinity for the indicator that can be used to further discriminate between competing ions.

The optical response of the indicator to the ion can be detected by various means that include measuring absorbance or fluorescence changes with an instrument, visually, or by use of a fluorescence sensing device. Several examples of fluorescence sensing devices are known, such as fluorometers, fluorescence microscopes, laser scanners, and flow cytometers as well as by cameras and other imaging equipment. These measurements may be made remotely by incorporation of the fluorescent ion sensor as part of a fiber optic probe. The indicator may be covalently attached to the fiber optic probe material, typically glass or functionalized glass (e.g., aminopropyl glass) or the indicator may be attached to the fiber optic probe via an intermediate polymer, such as polyacrylamide. The indicator solution may alternatively be incorporated non-covalently within a fiber optic probe, as long as there is a means whereby the target ion can come into contact with the indicator solution.

The ability of the compounds of the present invention to measure $Zn^{2+}$ concentrations in the presence of normal physiological concentrations of $Ca^{2+}$ and $Mg^{2+}$ allows the determination of $Zn^{2+}$ concentrations in and around cells and in cell extracts. Previous ion indicators have not exhibited sufficient discrimination between $Zn^{2+}$, $Ca^{2+}$ and $Mg^{2+}$ ions to allow the determination of $Zn^{2+}$ concentrations in living cells. The compounds of the present invention are useful for the discrimination of cells that contain high levels of $Zn^{2+}$ from other cells that do not contain high levels of $Zn^{2+}$. Such discrimination can be made visually, or instrumentally, and can be used to differentiate or sort cells by their internal $Zn^{2+}$ concentrations using fluorescence activated cell sorting, in conjunction with a flow cytometer.

In addition, the low response of the compounds of the present invention to $Ca^{2+}$ and $Mg^{2+}$ facilitates measurement of the transport, penetration or accumulation of heavy metals such as $Zn^{2+}$, $Pb^{2+}$, $Ba^{2+}$, $Cd^{2+}$, $Hg^{2+}$ and $La^{3+}$ into cells. Such ion transport may occur through diffusion, through pores or ion channels, or during the processes of cell death, lysis or fusion. An indicator of the present invention can be incorporated in a cell or a cell component, such as a liposome, that is essentially free of desired target metal ion, but that is then caused by some transport, fusion, lysis or other process to be made accessible to the target metal ion.

The examples below are given so as to illustrate the practice of this invention. They are not intended to limit or define the entire scope of the invention.

EXAMPLES

Example 1

Preparation of BTC 5'-nitro-BAPTA, tetramethyl ester (3):

5-formyl-4-hydroxy-5'-nitro-BAPTA tetramethyl ester (1) (500 mg, 0.79 mmol; as described in copending application 07/843,360, supra) is added to a solution of α-methyl benzothiazolyl acetate (2) (200 mg, 0.94 mmol; Iatridou et al., supra) in 5 mL methanol and 5 µL piperidine. The resulting solution is heated for one hour at 65° C. The resulting yellow precipitate was filtered and washed with 10 mL diethyl ether to give 528 mg (90%) of 3.

Example 2

Preparation of BTC 5'-nitro-BAPTA tetraacetic acid (4):

Compound 3 (75 mg, 0.1 mmol) is dissolved in 5 mL acetonitrile and LiI (400 mg, 3.0 mmol) is added in one portion. The resulting suspension is heated to reflux for 50 hours. After cooling, the resulting dark orange precipitate is filtered and washed with 5 mL acetonitrile and 5 mL acetone to give the tetralithium salt. The lithium salt is dissolved in 5 mL deionized water and the solution is acidified to pH 4 using 3 M HCl. The resulting orange solid is centrifuged and dried under vacuum to give pure 4 (95% yield).

Example 3

Preparation of BTC 5'-nitro-BAPTA, tetraacetoxymethyl ester (5):

Compound 4 (50 mg, 0.068 mmol) is dissolved in 5 mL acetonitrile and diisopropylethylamine (46 mg, 0.36 mmol) is added. The solution is stirred for 30 minutes followed by the addition of bromomethyl acetate (0.10 gm, 0.7 mmol) in one portion. The reaction is stirred for 2 hours at room temperature, after which the solvent is removed under reduced pressure. The resulting orange oil is suspended in 10 mL ethyl acetate and washed with 15 mL deionized water and 15 mL saturated NaCl. The organic layer is dried over $Na_2SO_4$ and evaporated under reduced pressure. The compound is further purified by column chromatography (40–60 μm $SiO_2$), eluting with a 1:1 ethyl acetate:hexanes. Column fractions containing pure 5 are combined and dried in vacuo to give 5 as a pure solid (75% yield).

Example 4

Preparation of Cyano-BTC 5'-nitro-BAPTA, tetramethyl ester (6):

Compound 3 (10 mg, 0.0126 mmol) is dissolved in 1 mL dry DMF and 0.1 mL of a 15 mg/mL solution of KCN (1.5 rag, 0.027 mmol) is added in one portion. The solution is stirred at 35° C. for 90 minutes, diluted mL chloroform and irradiated for 5 minutes using a 275 W sunlamp. Analysis using thin layer chromatography showed complete conversion of 3 to a red fluorescent product having a lower Rf. The product is further purified by column chromatography on silica gel (100 mL wet bed volume) eluting with 1:1:1 ethyl acetate: hexanes: $CHCl_3$. Fractions containing pure product are evaporated under reduced pressure to give a red oil.

Example 5.

Preparation of Cyano-BTC 5'-nitro-BAPTA, tetralithium salt (7):

Compound 6 (25 mg, 0.030 mmol) is dissolved in 3 mL dry acetonitrile and LiI (0.16 g, 1.21 mmol) is added in one portion. The red suspension is heated at reflux for 72 hours until the hydrolysis is complete as determined using thin layer chromatography. The reaction mixture is then cooled to 0° C. and centrifuged to give pure 7 as a red solid. The pellet is redissolved in water and purified using column chromatography on Sephadex® LH-20 eluting with pH 7.5 LiOH in deionized water. The product elutes as a red band, which is lyophilized to give 7 as a red powder (13.3 mg, 51% yield).

Example 6

Preparation of BOC 5'-nitro-BAPTA, tetramethyl ester (9)

Compound 1 (380 mg, 0.44 mmol) is dissolved in 3 mL dry methanol and 3 L piperidine. Ethyl α-benzoxazol acetate 8 (100 mg, 0.49 mmol, Iatridou, H. et.al.) is added in one portion and the reaction heated to reflux for 60 minutes. The reaction is cooled to 0° C., filtered and washed with 10 mL diethyl ether to give 290 Compound 9 (81% yield).

Example 7

Preparation of BOC 5'-nitro-BAPTA, tetralithium salt (10)

Compound 9 (100 mg, 0.12 mmol) is dissolved in 5 mL dry acetonitrile and LiI (0.96 gm, 7.2 mmol) is added in one portion. The suspension is stirred at reflux under nitrogen atmosphere for 96 hours. The reaction is then filtered and the isolated light yellow tetralithium salt is dissolved in 2 mL deionized water and purified on lipophilic Sephadex® LH-20 (100 mL wet bed volume) eluted with pH 7.5 LiOH. Column fractions containing pure product are combined, frozen and lyophilized to give 10 as a yellow powder.

Example 8

Fluorescence response of Compound 4 to increasing $Zn^{2+}$ concentration:

BTC 5'-nitro-BAPTA tetraacetic acid (Compound 4) is dissolved in 1.0 mL of pH 8.0 KOH in deionized water to give a dye solution with a concentration of approximately 1 mM. The dye solution is further diluted in deionized water at pH 7.0 to give a series of dye solutions with a dye concentration of 1 μM. Concentrated solutions of $ZnCl_2$ in water are added to each dye solution to give a series of solutions with $Zn^{2+}$ concentrations of between 0.1 and 25 μM. The solutions are excited by illumination at 415 nm and the fluorescence emission of each solution is scanned using a Hitachi-4500 spectrofluorometer. Emission intensities at 540 nm are plotted versus the ion concentration to give a calculated dissociation constant ($K_d$) for $Zn^{2+}$ of approximately 0.2 μM for Compound 4.

Example 9

Fluorescence response of Compound 4 to selected heavy metal ions: each

Compound 4 is diluted to a final concentration of 1 μM in separate solutions of selected metal ions, each having a metal ion concentration of 25 μM. The dye solutions are excited by illumination at 415 nm, and the fluorescence emission wavelengths and relative intensities are recorded. A solution of dye in 10 mM EGTA is scanned as an ion-free control. As shown in Table 1, the fluorescence emission wavelength of the indicator ranges from 503 nm in a 25 μM $Cd^{2+}$ solution to 528 nm in the absence of metal ions. The relative emission intensities are determined by arbitrarily assigning the fluorescence intensity of the 25 μM $Cd^{2+}$ solution to 1.0. The emission intensity increases approximately 50-fold from free indicator to $Cd^{2+}$ saturated indicator.

Example 10

Detection of $Zn^{2+}$ in rat cells with Compound 5:

Rat basophilic leukemia (RBL-2H3) cells ($10^6$ cells/mL) are incubated in modified Tyrode's buffer containing 0.1% bovine serum albumin plus either 5 μM BTC 5'-nitro-BAPTA acetoxymethyl ester (Compound 5) or 1 μM fura-2, acetoxymethyl ester for 60 minutes at 37° C. The cells are then pelleted by centrifugation at 1000× g for 10 minutes, then resuspended to a density of $10^6$ cells/mL in Tyrode's buffer containing 0.05 % gelatin. Aliquots of the Compound 5 or fura-2 loaded cell suspensions (2.5 mL) are then placed into 1 cm pathlength acrylic fluorescence cuvettes with small magnetic stir bars. Fluorescence measurements are performed in a fluorescence spectrophotometer (Photon Technologies Intl.) equipped with a magnetic stirrer. For fura-2 and Compound 5 measurements the excitation/emission monochromators are held at 340/520 nm or 430/525 rim, respectively. Additions are made to a single fura-2 preparation (panel A) and two different suspensions of Compound 5 loaded cells (panels B and C). Successive additions (indicated by arrows) were made to the cell suspensions as follows: (A) 2 μM Br-A23 187, 200 μM ZnCl$_2$, 50 mm CaCl$_2$. (B) 2 μM Br-A23 187, 200 μM ZnCl$_2$, 2 mM EDTA/4 mM Tris base. (C) 2 μM Br-A23187, 1 μM ZnCl$_2$, 0.1% Triton®X-100.

It is to be understood that, while the foregoing invention has been described in detail by way of illustration and example, numerous modifications, substitutions, and alterations are possible without departing from the spirit and scope of the invention as described in the following claims.

What is claimed is:

1. A compound of the formula:

[chemical structure]

wherein m is either 2 or 3;

R$^1$ is H, an alkyl group having 1–5 carbons, a benzyl, an alpha-acyloxyalkyl or a pharmaceutically acceptable esterifying group, a t-butyldimethylsilyl ester, or a pharmaceutically acceptable salt;

R$^2$, R$^3$, R$^4$ and R$^5$ are independently H or methyl;

R$^6$ is H, CN, CH$_3$, CF$_3$ or CONH$_2$;

X is O, S, or C(CH$_3$)$_2$;

Y is H, an alkyl having 1–18 carbons, —NO$_2$, —NH$_2$, —NH(C═O)(CH$_2$)$_n$CH$_3$, —CF$_3$, F, Cl, Br, I, —OR$^8$, —CO$_2$R$^9$, or —OCH$_2$CO$_2$R$^9$, where n=0–16; R$^8$ is H, an alkyl group having 1–18 carbons, a benzyl (C$_6$H$_5$CH$_2$—), and alpha-acyloxyalkyl, acetate, or a t-butyldimethylsilyl ether; and R$^9$ is H, an alkyl group having 1–17 carbons, a benzyl (C$_6$H$_5$CH$_2$—) an alpha-acyloxyalkyl or other pharmaceutically acceptable esterifying group, a t-butyldimethylsilyl ester, or a pharmaceutically acceptable salt; or Y is a covalently attached conjugant; and Z is one of H, an alkyl having 1–18 carbons, —NH$_2$, —NH(C═O)(CH$_2$)$_n$CH$_3$, —CF$_3$, F, Cl, Br, I, —OR$^8$, —CO$_2$R$^9$, or —OCH$_2$CO$_2$R$^9$; or Z is a covalently attached conjugant.

2. A compound as claimed in claim 1, wherein one of Y and Z is a covalently attached conjugant.

3. A compound as claimed in claim 2, wherein said covalently attached conjugant is a polymer film, a polymer microparticle, a dextran, or glass.

4. A compound as claimed in claim 1, wherein m=2.

5. A compound as claimed in claim 1, wherein R$^1$ and R$^9$ are acetoxymethyl esters, or R$^1$ is an acetoxymethyl ester and Y is H.

6. A compound as claimed in claim 1, wherein X is O or S.

7. A compound as claimed in claim 1, wherein R$^2$, R$^3$, R$^4$ and R$^5$ are each H.

8. A compound as claimed in claim 1, wherein R$^6$ is H or CN.

9. A method of detecting a polycationic metal ion in a sample, wherein said metal ion is Cd$^{2+}$, Hg$^{2+}$, Zn$^{2+}$, La$^{3+}$, Ba$^{2+}$, Tb$^{3+}$, Pb$^{2+}$, Bi$^{3+}$, Co$^{2+}$ or Al$^{3+}$, comprising:

a) adding to said sample, in an amount sufficient to generate a detectable fluorescent response to said metal ion, a compound according to the formula

[chemical structure]

wherein m is either 2 or 3;

R$^1$ is H, an alkyl group having 1–5 carbons, a benzyl, an alpha-acyloxyalkyl or a pharmaceutically acceptable esterifying group, a t-butyldimethylsilyl ester, or a pharmaceutically acceptable salt;

R$^2$, R$^3$, R$^4$ and R$^5$ are independently H or methyl;

R$^6$ is H, CN, CH$_3$, CF$_3$ or CONH$_2$;

X is O, S, or C(CH$_3$)$_2$;

Y is H, an alkyl having 1–18 carbons, —NO$_2$, —NH$_2$, —NH(C═O)(CH$_2$)$_n$CH$_3$, —CF$_3$, F, Cl, Br, I, —OR$^8$, —CO$_2$R$^9$, or —OCH$_2$CO$_2$R$^9$, where n=0–16; R$^8$ is H, an alkyl group having 1–18 carbons, a benzyl (C$_6$H$_5$CH$_2$—), an alpha-acyloxyalkyl, acetate, or a t-butyldimethylsilyl ether; and R$^9$ is H, an alkyl group having 1–17 carbons, a benzyl (C$_6$H$_5$CH$_2$—) an alpha-acyloxyalkyl or other pharmaceutically acceptable esterifying group, a t-butyldimethylsilyl ester, or a pharmaceutically acceptable salt; or Y is a covalently attached conjugant; and Z is one of H, an alkyl having 1–18 carbons, —NH$_2$, —NH(C═O)(CH$_2$)$_n$CH$_3$, —CF$_3$, F, Cl, Br, I, —OR$^8$, —CO$_2$R$^9$, or —OCH$_2$CO$_2$R$^9$; or Z is a covalently attached conjugant. b) illuminating said sample to generate an absorbance or fluorescence response; and c) observing said absorbance or fluorescence response.

10. A method, as claimed in claim 9, further comprising the step of determining the concentration of said metal ion.

11. A method, as claimed in claim 9, wherein the step of observing further comprises quantifying said absorbance or fluorescence response.

12. A method, as claimed in claim 11, wherein the step of observing is performed using a fluorometer, fluorescence microscope, laser scanner, or flow cytometer.

13. A method, as claimed in claim 9, wherein said metal ion is $Zn^{2+}$, $Pb^{2+}$, $Ba^{2+}$, $Cd^{2+}$, $Hg^{2+}$ and $La^{3+}$.

14. A method, as claimed in claim 13, wherein said metal ion is detected in the presence of physiological levels of $Ca^{2+}$ or $Mg^{2+}$.

15. A method, as claimed in claim 9, wherein said compound is present as part of a fiber optic probe.

16. A method, as claimed in claim 9, wherein said sample further comprises living cells or biological fluids.

* * * * *

UNITED STATES PATENT AND TRADEMARK OFFICE
CERTIFICATE OF CORRECTION

PATENT NO. : 5,459,276
DATED : October 17, 1995
INVENTOR(S) : Kuhn, et al.

It is certified that error appears in the above-indentified patent and that said Letters Patent is hereby corrected as shown below:

At column 1, line 49 "an" should be --and--.

At column 1, line 53 "benzofuranyoxy" should be --benzofuranyloxy--.
At column 1, line 53, "-2" (2nd occur.) should be deleted--.
At column 2, line 7 "$Pb^{2++}$" should be --$Pb^{2+}$--.

At column 2, line 38 "que" should be --quench--.

At column 3, line 37 "The invention" should be --The indicators of the present invention--.

At column 6, line 39 "other tar quantified" should be --other target ions that are typically detected or quantified--.

At column 7, line 26 "analyte is" should be --analyte concentration is--.

At column 9, line 29 "rag, 0.027" should be --mg, 0.027--.

At column 9, line 30 "diluted mL" should be --diluted with 5 mL--.

At column 9, line 33 "Rf" should be --$R_f$--.

At column 9, line 57 "3 L" should be --3 µL--.

At column 9, line 57 "α-benzoxazol" should be --α-benzoxazolyl--.

UNITED STATES PATENT AND TRADEMARK OFFICE
CERTIFICATE OF CORRECTION

PATENT NO. : 5,459,276
DATED : October 17, 1995
INVENTOR(S) : Kuhn, et al.

Page 2 of 2

It is certified that error appears in the above-indentified patent and that said Letters Patent is hereby corrected as shown below:

At column 9, line 61 "290 compound" should be --290 mg Compound--.

At column 10, line 29 "metal ions: each" should be --metal ions:--.

At column 10, line 63 "rim," should be --nm,--.

At column 10, line 67 "Br-A23 187" should be --Br-A23187--.

At column 11, line 1 "Br-A23 187" should be --Br-A23187--.

Signed and Sealed this

Twenty-second Day of October, 1996

Attest:

BRUCE LEHMAN

Attesting Officer

Commissioner of Patents and Trademarks